US012734120B2

(12) United States Patent
Moharir

(10) Patent No.: US 12,734,120 B2
(45) Date of Patent: Sep. 15, 2026

(54) CLEANING COMPOSITION

(71) Applicant: NUTRITIONAL CONSULTANTS UNLIMITED, INC., Mesa, AZ (US)

(72) Inventor: Yadunath Moharir, Mesa, AZ (US)

(73) Assignee: NUTRITIONAL CONSULTANTS UNLIMITED, INC., Mesa, AZ (US)

( * ) Notice: Subject to any disclaimer, the term of this patent is extended or adjusted under 35 U.S.C. 154(b) by 558 days.

(21) Appl. No.: 18/106,938

(22) Filed: Feb. 7, 2023

(65) Prior Publication Data

US 2023/0181434 A1 Jun. 15, 2023

(51) Int. Cl.

| | |
|---|---|
| ***A61K 8/36*** | (2006.01) |
| ***A61K 8/73*** | (2006.01) |
| ***A61K 8/81*** | (2006.01) |
| ***A61Q 19/10*** | (2006.01) |

(52) U.S. Cl.

CPC .............. *A61K 8/361* (2013.01); *A61K 8/736* (2013.01); *A61K 8/8111* (2013.01); *A61Q 19/10* (2013.01); *A61K 2800/51* (2013.01); *A61K 2800/596* (2013.01)

(58) Field of Classification Search

None

See application file for complete search history.

(56) References Cited

U.S. PATENT DOCUMENTS

| | | | | |
|---|---|---|---|---|
| 6,017,517 | A | 1/2000 | Park | |
| 9,006,162 | B1 | 4/2015 | Rizk | |
| 10,039,939 | B2 | 8/2018 | Xavier | |
| 10,806,769 | B2 | 10/2020 | Tian | |
| 11,123,276 | B2 | 9/2021 | Liang | |
| 2003/0157047 | A1 | 8/2003 | Lennon | |
| 2016/0089322 | A1 | 3/2016 | Santos Nogueira | |
| 2021/0236393 | A1* | 8/2021 | Story | A61K 8/0216 |
| 2023/0270633 | A1* | 8/2023 | Liu | C11D 3/323 424/401 |

FOREIGN PATENT DOCUMENTS

| | | | | |
|---|---|---|---|---|
| WO | WO-2016010474 | A1 * | 1/2016 | C11D 7/266 |

OTHER PUBLICATIONS

Stepan "Boundless Creativity" <https://www.stepan.com/content/dam/stepan-dot-com/webdam/website-product-documents/literature/household-institutional-industrial-cleaning/HomeCareSolidFormulationGuidance.pdf> (Year: 2022).*

SpecialChem "Lauramidopropyl Betaine" <https://www.specialchem.com/cosmetics/inci-ingredients/lauramidopropyl-betaine> (Year: 2025).*

Mike Efting "Sunflower lecithin meets growing demand for clean-label ingredients" Supply Side Food & Beverage Journal <https://www.supplysidefbj.com/fat-oils/sunflower-lecithin-a-formidable-emulsifier> (Year: 2021).*

* cited by examiner

*Primary Examiner* — Nicole P Babson

(74) *Attorney, Agent, or Firm* — Cooper Legal Group, LLC

(57) ABSTRACT

The present invention provides a cleaning composition for contact or non-contact surface comprising: a water-soluble surfactant; a medium chain triglyceride (MCT); a non-ionic surfactant; an emulsifying agent; a wetting agent; and a maltodextrin. The present invention also discloses a method for cleaning the contact or non-contact surface in the manufacturing area where turmeric gets processed. In another embodiment, the cleaning composition for skin or nails comprising: a water-soluble surfactant; a medium chain triglyceride (MCT); a non-ionic surfactant; an emulsifying agent; a wetting agent; a thickening agent; an adsorbent; an oxidizer; and a maltodextrin is disclosed. The method for cleaning the skin or nails is also disclosed in the present invention.

8 Claims, No Drawings

CLEANING COMPOSITION

TECHNICAL FIELD

The present invention relates generally to a chemical composition, and in particular relates to the cleaning composition for removing stains from contact or non-contact surfaces and method for cleaning contact or non-contact surfaces in the manufacturing area where turmeric gets processed. The present invention further relates to the cleaning composition for removing stains from skin or nails and method for cleaning skin or nails.

BACKGROUND

Curcumin is a principle curcuminoids present in the turmeric plant apart from other two curcuminoids viz demethoxycurcumin and bis demethoxycurcumin. Curcumin is a diarylheptanoid belonging to the group of curcuminoids, which are phenolic pigments present in the turmeric. Turmeric is obtained from the rhizome of *Curcuma longa linn*. belonging to the natural order Zingiberaceae. Turmeric is also known as *Curcuma*, Curcumin, Halada, Haldi, *Haridra*, Indian Saffron, Nisha, *Pian* Jiang *Huang, Rajani, Safran* Bourbon, *Safran* de Batallita, *Safran* des Indes, Turmeric Root, and *Yu Jin*.

Curcumin is a bright yellow chemical produced in the turmeric rhizome. The phenolic pigment, curcumin present in the turmeric is responsible for the bright yellow color of turmeric.

Typically, once the production of turmeric powder is completed, the after-productions operations such as cleaning the machines that are used in production and cleaning the area of manufacturing has to be done with proper care and hygiene. The turmeric processing plant faces the major difficulty in cleaning of the processing machines and the processing surfaces after manufacturing of turmeric products. Being light in weight, the turmeric powder can easily flow and stain the surrounding area including walls and floors of the manufacturing unit. The equipment used for preparing the turmeric powder can also easily get stained due to strong yellow color of the turmeric. The yellow color of curcumin is the most stubborn stain and cleaning of this yellow color stain is found to be extremely difficult in the turmeric processing plant.

The prior art discloses the use of Sodium hydroxide (5N-10 N), followed by water and then using isopropyl alcohol for cleaning the contact or non-contact surfaces in the dietary supplement industry. WO2002062935 discloses application of oxidizing agent and exposing the stained area to ultraviolet wavelength for removing the turmeric stains is also listed in the prior art. JP2016533412A discloses use of alkylene-styrene copolymers comprising agents to clean the hard or soft surfaces. The combination of citric acid, sodium chloride and sodium hypochlorite for cleaning the turmeric stain from fabric is disclosed in IN201941049844.

The conventional detergent or the cleaning agent used for cleaning the turmeric-stained surfaces are underperforming and time consuming. The generic cleaner lacks the capability to trap and suspend the turmeric pigment and which leads to redeposition of the pigments on the surfaces, it results in need of re-cleaning the surfaces multiple times. The underperformance of the cleaning composition cause impact on overall production capacity and thus economy of the production unit.

Hence there arises a need in present state of art to develop a chemical composition and method to clean the contact or non-contact surfaces in the turmeric production unit, which is safe, effective and economical.

Various conventional methods are used to remove the turmeric stains from skin and nails. Baking powder, lemon juice, vinegar or hydrogen peroxide is commonly used to clean the hands and nails covered with turmeric stain. However, these conventional methods do not prove to be effective and does not remove the stain completely.

Therefore, there remains a need to develop a cleaning composition for skin and nails which is not harsh to the skin and effectively cleans the skin and nails.

SUMMARY

Embodiments of the present invention present technological improvements as solutions to one or more of the above-mentioned technical problems.

This summary is provided to introduce aspects related to cleaning composition. This summary is not intended to identify essential features of the claimed invention nor it is intended for use in determining or limiting the scope of the present invention.

The present invention relating to the chemical composition for cleaning the contact or non-contact surface as well as method for cleaning the contact or non-contact surfaces, the present invention further relates to the cleaning composition for skin or nails and the method for cleaning skin or nails, it is to be understood that this application is not limited to the particular system(s) and methodologies described, as there can be multiple possible embodiments which are not expressly illustrated in the present invention. It is also to be understood that the terminology used in the description is for the purpose of describing the implementations or versions or embodiments only and is not intended to limit the scope of the present invention.

In one of the embodiments, the present invention discloses cleaning composition for contact or non-contact surface comprising: a water-soluble surfactant; a medium chain triglyceride (MCT); a non-ionic surfactant; an emulsifying agent; a wetting agent, and a maltodextrin, wherein the water-soluble surfactant is in the range of 0.02%-10% (weight(w)/weight (w)); the MCT is in the range of 0.01%-10% (w/w); the non-ionic surfactant is in the range of 0.01%-7% (w/w); the emulsifying agent is in the range of 0.2%-47% (w/w); the wetting agent is in the range of 0.05%-35% (w/w); and the maltodextrin is in the range of 0.1%-40% (w/w).

In another embodiments, there is provided a method for cleaning the contact or non-contact surface, the method comprising: mixing a water-soluble surfactant, a medium chain triglyceride (MCT), a non-ionic surfactant, an emulsifying agent, a wetting agent, and a maltodextrin; obtaining a powder composition; adding a hot water with a temperature in the range of 40 degrees Celsius to 50 degrees Celsius in the powder composition for obtaining a cleaning solution; applying the cleaning solution on the surface; and mopping the surface after application of the cleaning solution.

In yet another embodiment, the present invention discloses a cleaning composition for skin or nails comprising: a water-soluble surfactant; a medium chain triglyceride (MCT); a non-ionic surfactant; an emulsifying agent; a wetting agent; a thickening agent; an adsorbent; an oxidizer; and a maltodextrin, wherein the water-soluble surfactant is in the range of 0.02%-10% (weight(w)/weight (w)); the MCT is in the range of 0.01%-10% (w/w); the non-ionic surfactant is in the range of 0.01%-7% (w/w); the emulsifying agent is in the range of 0.2%-47% (w/w); the wetting agent is in the range of 0.05%-35% (w/w); the thickening agent is in the range of 0.02%-20% (w/w); the maltodextrin is in the range of 0.1%-40% (w/w); the adsorbent is in the range of 0.01%-10% (w/w), the adsorbent includes calcium carbonate in the range of 0.1%-10% and calcium lactate in the range of 0.1%-10%; and the oxidizer is in the range of 0.01%-2% (w/w).

In another embodiment, there is provided a method for cleaning the skin or nails comprising: mixing a water-soluble surfactant, a medium chain triglyceride (MCT), a non-ionic surfactant, an emulsifying agent, a wetting agent, a thickening agent, an adsorbent, an oxidizer, and maltodextrin; obtaining a powder composition; adding a hot water with a temperature in the range of 40 degrees Celsius to 50 degrees Celsius in the powder composition for obtaining a cleaning solution; applying the cleaning solution on the skin or nails; and washing the skin or nails after application of the cleaning solution.

Additional aspects, advantages, features and objects of the present invention would be made apparent from the detailed description of the illustrative embodiments. It will be appreciated that features of the present invention are susceptible to being combined in various combinations without departing from the scope of the present invention as defined by the below mentioned detailed description.

DETAILED DESCRIPTION

The invention will now be described with reference to the accompanying embodiments which do not limit the scope and ambit of the invention. The description provided is purely by way of example and illustration.

The embodiments herein and the various features and advantageous details thereof are explained with reference to the non-limiting embodiments in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

Some embodiments of this invention, illustrating all its features, will now be discussed in detail. The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Ratios, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a concentration range of about 0.01-10% should be interpreted to include not only the explicitly recited limits of about 0.01% to about 10% but also to include sub-ranges, such as 1-9%, 1.5-9.5% and so forth, as well as individual amounts, including fractional amounts, within the specified ranges, such as 1.25%, and 5.55% for example.

The term "surfactant" used herein refers to wetting agents or surface acting agents that can form amphipathic micelles which lower the liquid-liquid or liquid-solid surface tension.

The term "emulsifying agent" used herein refers to compound or substances that make the solution stable i.e., preventing the individual elements from separating.

The term "wetting agent" used herein refers to compound or substances that lowers the surface tension of aqueous solutions, thereby, enhance the wetting of surfaces and also increases the spreading and penetrating properties of a liquid.

The term "adsorbent" used herein refers to solid substances used to collect solute molecules from liquid.

The term "oxidizer" used herein refers to substance that oxidizes another sub stance.

The term "contact surfaces" used herein refers to all surfaces that may come in contact with food products during production, processing, and packaging. For the purpose of the present disclosure, contact surface may be selected from, but not limited to utensils, pots, pans, mixing bowls, mixers and blenders.

The term "non-contact surfaces" used herein refers to floors, walls that do not come in direct contact with the food products during production but may get contaminated with indirect flow of food product.

The term "cleaning" used herein refers to disinfecting, sterilizing, and removal of soil, grease, and grime from the surface of any object.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, the preferred methods, and materials are now described.

The conventional detergent or the cleaning agent used for cleaning the turmeric surface are underperforming and time consuming. The generic cleaner lacks the capability to trap and suspend the turmeric pigment and which leads to redeposition of the pigments on surfaces, it results in re-cleaning the surfaces multiple times. The underperformance of the cleaning composition cause impact on overall production capacity and thus economy of the production unit.

In an aspect of the present invention, in order to overcome the above referenced problems and to provide various advantages elaborated in the subsequent section, a chemical composition for cleaning contact or non-contact surfaces as well as method for cleaning the contact or non-contact surface is disclosed. The present invention also discloses the cleaning composition for skin or nails and method for cleaning the skin or nails.

In the following description, for the purpose of explanation, specific details are set forth in order to provide an understanding of the present invention. It will be apparent, however, to one skilled in the art that the present invention may be practiced without these details. One skilled in the art will recognize that embodiments of the present invention, some of which are described below, may be incorporated into a number of systems.

In view of above, the present invention relates to the cleaning composition for contact or non-contact surfaces, comprising combination of a water-soluble surfactant; a medium chain triglyceride (MCT); a non-ionic surfactant; an emulsifying agent; a wetting agent, and a maltodextrin. The water-soluble surfactant such as polyethylene glycol (PEG) helps to disperse the insoluble curcuminoids evenly in the medium chain triglycerides (MCT). The addition of non-ionic surfactant such as polysorbate 20 or polysorbate 80, being more stable and nontoxic is useful in combination with the water soluble surfactant to remove the curcumin from the contact or non-contact surfaces. The other ingredients used in the composition such as sunflower lecithin is works as an emulsifying agent, the sunflower lecithin homogenizes the liquid mixtures and helps in repelling the sticking material from surfaces. The sun-flower lecithin is offering a special feature that it is hypo allergenic and safe to use in the food industries due to fact that more and more people are prone to have allergic reaction. The wetting agent such as sodium lauryl sulfoacetate, lowers the surface tension of aqueous solutions, thereby, enhance the wetting of surfaces. It also acts as foaming agent. The use of medium chain triglycerides plays a key role in the present composition. MCT keeps the turmeric in solution that floats on the water and keeps away from going back and sticking to the surface of the Floor or the Walls. Insoluble turmeric gets dissolved in MCT and it floats on the water surface. Maltodextrin present in the composition acts as a carrier for mixing of all the ingredient evenly.

The cleaning composition for skin or nails as disclosed in the present invention, comprises combination of a water-soluble surfactant; a medium chain triglyceride (MCT); a non-ionic surfactant; an emulsifying agent; a wetting agent; a thickening agent; an adsorbent; an oxidizer; and a maltodextrin. In addition to the component disclosed in the composition for cleaning contact or non-contact surfaces, the cleaning composition for skin or nails has adsorbent as an important ingredient. The adsorbent such as calcium carbonate and calcium lactate work as a substrate for turmeric to bind as it gets released from hands and nail as turmeric has an affinity to bind with Calcium. Another key ingredient of this composition, the oxidizer helps in oxidizing the yellow color of the curcumin, thus remove the yellow stain from the skin or nails. The use of sodium percarbonate has found to be an effective oxidizer in this composition and turns curcuminoids to white coloration.

In one of the embodiments, the present invention discloses a cleaning composition for contact or non-contact surface comprising: a water-soluble surfactant; a medium chain triglyceride (MCT); a non-ionic surfactant; an emulsifying agent; a wetting agent, and a maltodextrin, wherein the water-soluble surfactant is in the range of 0.02%-10% (weight(w)/weight (w)); the MCT is in the range of 0.01%-10% (w/w); the non-ionic surfactant is in the range of 0.01%-7% (w/w); the emulsifying agent is in the range of 0.2%-47% (w/w); the wetting agent is in the range of 0.05%-35% (w/w); and the maltodextrin is in the range of 0.1%-40% (w/w).

In another embodiments, a method for cleaning the contact or non-contact surface, the method comprising: mixing a water-soluble surfactant, a medium chain triglyceride (MCT), a non-ionic surfactant, an emulsifying agent, a wetting agent, and a maltodextrin; obtaining a powder composition; adding a hot water with a temperature in the range of 40 degrees Celsius to 50 degrees Celsius in the powder composition for obtaining a cleaning solution; applying the cleaning solution on the surface; and mopping the surface after application of the cleaning solution.

In another implementation, the water-soluble surfactant is polyethylene glycol (PEG).

In another implementation, the non-ionic surfactant is selected from the group consisting of ethoxylated amines, ethoxylated alcohol, ethoxylated, and alkoxylated fatty acids.

In another implementation, the non-ionic surfactant is polysorbate-20 or polysorbate-80.

In another implementation, the emulsifying agent is selected from the group consisting of anionic emulsifying agents, cationic emulsifying agents, nonionic emulsifying agents, natural emulsifying agents, finely dispersed solids emulsifying agents, and auxiliary emulsifying agents.

In another implementation, the emulsifying agent is sun flower lecithin.

In another implementation, the wetting agent is selected from the group consisting of anionic wetting agents, cationic wetting agents, amphoteric wetting agents, and nonionic method wetting agents.

In another implementation, the wetting agent is sodium lauryl sulfoacetate.

In another embodiment, the present invention discloses a cleaning composition for skin or nails comprising: a water-soluble surfactant; a medium chain triglyceride (MCT); a non-ionic surfactant; an emulsifying agent; a wetting agent; a thickening agent; an adsorbent; an oxidizer; and a maltodextrin, wherein the water-soluble surfactant is in the range of 0.02%-10% (weight(w)/weight (w)); the MCT is in the range of 0.01%-10% (w/w); the non-ionic surfactant is in the range of 0.01%-7% (w/w); the emulsifying agent is in the range of 0.2%-47% (w/w); the wetting agent is in the range of 0.05%-35% (w/w); the thickening agent is in the range of 0.02%-20% (w/w); the maltodextrin is in the range of 0.1%-40% (w/w); the adsorbent is in the range of 0.01%-10% (w/w), the adsorbent includes calcium carbonate in the range of 0.1%-10% and calcium lactate in the range of 0.1%-10%; and the oxidizer is in the range of 0.01%-2% (w/w).

In another embodiment, there is provided a method for cleaning the skin or nails comprising: mixing a water-soluble surfactant, a medium chain triglyceride (MCT), a non-ionic surfactant, an emulsifying agent, a wetting agent, a thickening agent, an adsorbent, a oxidizer, and a maltodextrin; obtaining a powder composition; adding a hot water with a temperature in the range of 40 degrees Celsius to 50 degrees Celsius in the powder composition for obtaining a cleaning solution; applying the cleaning solution on the skin or nails; and washing the skin or nails after application of the cleaning solution.

In another implementation, the thickening agent is selected from the group consisting of hydrocolloid thickeners including starch, xanthan, guar gum, locust bean gum, gum karaya, gum tragacanth, gum arabic, and cellulose derivatives.

In another implementation, the thickening agent is Hydroxypropyl Methyl Cellulose (HPMC).

In another implementation, the adsorbent includes calcium carbonate and calcium lactate.

In another implementation, the oxidizer is sodium percarbonate.

The present invention is further described in light of the following experiments which are set forth for an illustration purpose only and not to be construed for limiting the scope of the invention. The following experiments can be scaled up to industrial/commercial scale and the results obtained can be extrapolated to industrial scale.

Example 1

Process of Preparing the Cleaning Composition-1 for Contact or Non-Contact Surface The cleaning composition for contact or non-contact surface was prepared as per the present disclosure at a room temperature and atmospheric pressure. The components of the composition as disclosed in Table 1 were used to prepare the composition according to its weight ranges. The weight percentages of the components were calculated with respect to total weight of the composition.

TABLE 1

| Category | Component | % (w/w) | % range (w/w) |
|---|---|---|---|
| Water-soluble surfactant | polyethylene glycol (PEG) | 3.0 | 0.02-10 |
| | medium chain triglyceride (MCT) | 6.9 | 0.01-10 |
| Non-ionic surfactant | polysorbate-80 | 3.5 | 0.01-7 |
| Emulsifying agent | sun flower lecithin | 35.0 | 0.2-47 |
| Wetting agent | sodium lauryl sulfoacetate | 15.0 | 0.05-35 |
| Carrier | maltodextrin | 36.6 | 0.1-40 |

Firstly, 3.0% (w/w) of polyethylene glycol (PEG), 6.9% (w/w) of medium chain triglyceride (MCT), 3.5% (w/w) of polysorbate 80, 35% (w/w) of sunflower lecithin, 15% (w/w) of sodium lauryl sulfoacetate and 36.6% (w/w) of maltodextrin were mixed together to obtain the powder composition. Then 4 liters of a hot water with a temperature in the range of 40 degrees Celsius to 50 degrees Celsius was added in the powder composition to get the cleaning solution. This cleaning solution was further subjected to the test for cleaning efficacy.

Example 2

Process of Preparing the Cleaning Composition-2 for Contact or Non-Contact Surface The cleaning composition for contact or non-contact surface was prepared as per the present disclosure at a room temperature and atmospheric pressure. The components of the composition as disclosed in Table 2 were used to prepare the composition according to its weight ranges. The weight percentages of the components were calculated with respect to total weight of the composition.

TABLE 2

| Category | Component | % (w/w) | % range (w/w) |
|---|---|---|---|
| Water-soluble surfactant | polyethylene glycol (PEG) | 3.6 | 0.02-10 |
| | medium chain triglyceride (MCT) | 7.2 | 0.01-10 |
| Non-ionic surfactant | polysorbate-20 | 3.6 | 0.01-7 |
| Emulsifying agent | sun flower lecithin | 36.1 | 0.2-47 |
| Wetting agent | sodium lauryl sulfoacetate | 18.1 | 0.05-35 |
| Carrier | maltodextrin | 31.4 | 0.1-40 |

Firstly, 3.6% (w/w) of polyethylene glycol (PEG), 7.2% (w/w) of medium chain triglyceride (MCT), 3.6% (w/w) of polysorbate 20, 36.1% (w/w) of sunflower lecithin, 18.1% (w/w) of sodium lauryl sulfoacetate and 31.4% (w/w) of maltodextrin were mixed together to obtain the powder composition. Then 4 liters of a hot water with a temperature in the range of 40 degrees Celsius to 50 degrees Celsius was added in the powder composition to get the cleaning solution. This cleaning solution was further subjected to the test for cleaning efficacy.

Example 3

Process of Preparing the Cleaning Composition-3 for Contact or Non-Contact Surface The cleaning composition for contact or non-contact surface was prepared as per the present disclosure at a room temperature and atmospheric pressure. The components of the composition as disclosed in Table 3 were used to prepare the composition according to its weight ranges. The weight percentages of the components were calculated with respect to total weight of the composition.

TABLE 3

| Category | Component | % (w/w) | % range (w/w) |
|---|---|---|---|
| Water-soluble surfactant | polyethylene glycol (PEG) | 4.1 | 0.02-10 |
| | medium chain triglyceride (MCT) | 7.8 | 0.01-10 |
| Non-ionic surfactant | polysorbate-80 | 4.0 | 0.01-7 |
| Emulsifying agent | sun flower lecithin | 37.0 | 0.2-47 |
| Wetting agent | sodium lauryl sulfoacetate | 17.9 | 0.05-35 |
| Carrier | maltodextrin | 29.2 | 0.1-40 |

Firstly, 4.1% (w/w) of polyethylene glycol (PEG), 7.8% (w/w) of medium chain triglyceride (MCT), 4.0% (w/w) of polysorbate 80, 37.0% (w/w) of sunflower lecithin, 17.9% (w/w) of sodium lauryl sulfoacetate and 29.2% (w/w) of maltodextrin were mixed together to obtain the powder composition. Then 4 liters of a hot water with a temperature in the range of 40 degrees Celsius to 50 degrees Celsius was added in the powder composition to get the cleaning solution. This cleaning solution was further subjected to the test for cleaning efficacy.

Example 4

Assessment of Cleaning Efficacy of Composition 1, Composition 2 and Composition 3.

The cleaning efficacy of composition 1, composition 2 and composition 3 for contact or non-contact surface was assessed against the floor covered with the turmeric stain. The turmeric-stained covered floor was treated with the composition 1, composition 2, and composition 3. The compositions prepared as per example 1, example 2 and example 3 was applied on the floor to be cleaned and then mopped immediately with the mopping tool.

The cleaning effect was evident from the visual color difference between the floor before treatment and floor after treatment. The floor stained with turmeric color when treated with composition 1 shows that 75%-80% of stains were cleaned. It was observed that 90%-99% of the turmeric stained were cleaned from the floor treated with composition 2. Whereas, when the floor was treated with composition 3, 85%-90% stains were removed from the floor.

Example 5

Process of Preparing the Cleaning Composition-4 for Skin or Nails

The cleaning composition for skin or nails was prepared as per the present disclosure at a room temperature and atmospheric pressure. The components of the composition as disclosed in Table 4 were used to prepare the composition according to its weight ranges. The weight percentages of the components were calculated with respect to total weight of the composition.

TABLE 4

| Category | Component | % (w/w) | % range (w/w) |
|---|---|---|---|
| Water-soluble surfactant | polyethylene glycol (PEG) | 2.6 | 0.02-10 |
| | medium chain triglyceride (MCT) | 5.3 | 0.01-10 |
| Non-ionic surfactant | polysorbate-80 | 2.6 | 0.01-7 |
| Emulsifying agent | sun flower lecithin | 26.4 | 0.2-47 |
| Wetting agent | sodium lauryl sulfoacetate | 13.2 | 0.05-35 |
| Carrier | maltodextrin | 22.9 | 0.1-40 |
| Thickening agent | Hydroxypropyl Methyl Cellulose | 15.8 | 0.02-20 |
| Adsorbent | Calcium carbonate | 5.3 | 0.1-10 |
| Adsorbent | Calcium lactate | 5.3 | 0.1-10 |
| Oxidizer | Sodium percarbonate | 0.5 | 0.01-2 |

Firstly, 2.6% (w/w) of polyethylene glycol (PEG), 5.3% (w/w) of medium chain triglyceride (MCT), 2.6% (w/w) of polysorbate 80, 26.4% (w/w) of sunflower lecithin, 13.2% (w/w) of sodium lauryl sulfoacetate, 22.9% (w/w) of maltodextrin, 15.8% (w/w) of Hydroxypropyl Methyl Cellulose, 5.3% (w/w) of Calcium carbonate, 5.3% (w/w) of Calcium lactate and 0.5% (w/w) of Sodium percarbonate were mixed together to obtain the powder composition. Then 500 ml of a hot water with a temperature in the range of 40 degrees Celsius to 50 degrees Celsius was added in the powder composition to get the cleaning solution. This cleaning solution was further subjected to the test for cleaning efficacy.

Example 6

Process of Preparing the Cleaning Composition-5 for Skin or Nails

The cleaning composition for skin or nails was prepared as per the present disclosure at a room temperature and atmospheric pressure. The components of the composition as disclosed in Table 5 were used to prepare the composition according to its weight ranges. The weight percentages of the components were calculated with respect to total weight of the composition.

TABLE 5

| Category | Component | % (w/w) | % range (w/w) |
|---|---|---|---|
| Water-soluble surfactant | polyethylene glycol (PEG) | 3.1 | 0.02-10 |
| | medium chain triglyceride (MCT) | 4.9 | 0.01-10 |
| Non-ionic surfactant | polysorbate-20 | 3.0 | 0.01-7 |
| Emulsifying agent | sun flower lecithin | 27.1 | 0.2-47 |
| Wetting agent | sodium lauryl sulfoacetate | 11.2 | 0.05-35 |
| Carrier | maltodextrin | 24.9 | 0.1-40 |
| Thickening agent | Hydroxypropyl Methyl Cellulose | 16.0 | 0.02-20 |
| Adsorbent | Calcium carbonate | 4.5 | 0.1-10 |
| Adsorbent | Calcium lactate | 4.5 | 0.1-10 |
| Oxidizer | Sodium percarbonate | 0.7 | 0.01-2 |

Firstly, 3.1% (w/w) of polyethylene glycol (PEG), 4.9% (w/w) of medium chain triglyceride (MCT), 3.0% (w/w) of polysorbate 20, 27.1% (w/w) of sunflower lecithin, 11.2% (w/w) of sodium lauryl sulfoacetate, 24.9% (w/w) of maltodextrin, 16.0% (w/w) of Hydroxypropyl Methyl Cellulose, 4.5% (w/w) of Calcium carbonate, 4.5% (w/w) of Calcium lactate and 0.7% (w/w) of Sodium percarbonate were mixed together to obtain the powder composition. Then 500 ml of a hot water with a temperature in the range of 40 degrees Celsius to 50 degrees Celsius was added in the powder composition to get the cleaning solution. This cleaning solution was further subjected to the test for cleaning efficacy.

Example 7

Process of Preparing the Cleaning Composition-6 for Skin or Nails

The cleaning composition for skin or nails was prepared as per the present disclosure at a room temperature and atmospheric pressure. The components of the composition as disclosed in Table 6 were used to prepare the composition according to its weight ranges. The weight percentages of the components were calculated with respect to total weight of the composition.

TABLE 6

| Category | Component | % (w/w) | % range (w/w) |
|---|---|---|---|
| water-soluble surfactant | polyethylene glycol (PEG) | 3.5 | 0.02-10 |
| | medium chain triglyceride (MCT) | 5.9 | 0.01-10 |
| non-ionic surfactant | polysorbate-80 | 4.8 | 0.01-7 |
| emulsifying agent | sun flower lecithin. | 20.0 | 0.2-47 |
| wetting agent | sodium lauryl sulfoacetate | 12.9 | 0.05-35 |
| Carrier | maltodextrin | 20.7 | 0.1-40 |
| Thickening agent | Hydroxypropyl Methyl Cellulose | 18.0 | 0.02-20 |
| Adsorbent | Calcium carbonate | 7.0 | 0.1-10 |
| Adsorbent | Calcium lactate | 7.0 | 0.1-10 |
| Oxidizer | Sodium percarbonate | 0.2 | 0.01-2 |

Firstly, 3.5% (w/w) of polyethylene glycol (PEG), 5.9% (w/w) of medium chain triglyceride (MCT), 4.8% (w/w) of polysorbate 80, 20.0% (w/w) of sunflower lecithin, 12.9% (w/w) of sodium lauryl sulfoacetate, 20.7% (w/w) of maltodextrin, 18.0% (w/w) of Hydroxypropyl Methyl Cellulose, 7.0% (w/w) of Calcium carbonate, 7.0% (w/w) of Calcium lactate and 0.2% (w/w) of Sodium percarbonate were mixed together to obtain the powder composition. Then 500 ml of a hot water with a temperature in the range of 40 degrees Celsius to 50 degrees Celsius was added in the powder composition to get the cleaning solution. This cleaning solution was further subjected to the test for cleaning efficacy.

Example 8

Assessment of Cleaning Efficacy of Composition 4, Composition 5 and Composition 6.

The cleaning efficacy of composition 4, composition 5 and composition 6 for skin or nails was assessed against the skin and nail surfaces stained with the turmeric stain. The turmeric-stained covered skin or nails were treated with the composition 4, composition 5, and composition 6. The compositions prepared as per example 5, example 6 and example 7 was applied to the skin or nails to be cleaned and then wiped immediately with the clean cloth.

The cleaning effect was evident from the visual color difference between the skin or nails before the treatment and after the treatment of composition. It was observed that 95%-99% of the turmeric stains were cleaned from the skin or nail surface treated with composition 4. The skin or nails treated with composition 5 shows that 80%-90% of turmeric stains were cleaned. Whereas, it was observed that 75%-85% of turmeric stains were removed from the skin or nails treated with composition 6.

The claimed subject matter of the cleaning composition and method therefor, in a preferred embodiment is created for cleaning or removing or diluting or scrubbing stains of turmeric from contact or non-contact surfaces such as equipment's used for processing or treating turmeric composition and surrounding areas including, platform or stand, floors and walls. Also, the claimed subject matter of the cleaning composition and method therefor, in a preferred embodiment is created for cleaning or removing or diluting or scrubbing stains of turmeric from skin and/or nails and/or any other body parts.

It should be noted that the description merely illustrates the principles of the present invention. It will thus be appreciated that those skilled in the art will be able to devise various arrangements that, although not explicitly described herein, embody the principles of the present invention. Furthermore, all examples recited herein are principally intended expressly to be only for explanatory purposes to help the reader in understanding the principles of the invention and the concepts contributed by the inventor to furthering the art, and are to be construed as being without limitation to such specifically recited examples and conditions. Moreover, all statements herein reciting principles, aspects, and embodiments of the invention, as well as specific examples thereof, are intended to encompass equivalents thereof.

The invention claimed is:

1. A cleaning composition for contact or non-contact surface of a turmeric production unit comprising:

a water-soluble surfactant;

a medium chain triglyceride (MCT);

a non-ionic surfactant;

an emulsifying agent;

a wetting agent; and a maltodextrin, wherein the cleaning composition comprises:

3.6% (weight (w)/weight (w)) of the water-soluble surfactant;

7.2% (w/w) of the MCT;

3.6% (w/w) of the non-ionic surfactant;

36.1% (w/w) of the emulsifying agent;

18.1% (w/w) of the wetting agent; and 31.4% (w/w) of the maltodextrin, wherein the cleaning composition is mixed with water at a temperature of 40° C. to 50° C. to form a cleaning solution that provides improved removal of turmeric-derived stains.

2. The cleaning composition of claim 1, wherein the water-soluble surfactant is polyethylene glycol (PEG).

3. The cleaning composition of claim 1, wherein the non-ionic surfactant is selected from the group consisting of ethoxylated amines, ethoxylated alcohol, ethoxylated, and alkoxylated fatty acids.

4. The cleaning composition of claim 1, wherein the non-ionic surfactant is polysorbate-20 or polysorbate-80.

5. The cleaning composition of claim 1, wherein the emulsifying agent is selected from the group consisting of anionic emulsifying agents, cationic emulsifying agents, nonionic emulsifying agents, natural emulsifying agents, finely dispersed solids emulsifying agents, and auxiliary emulsifying agents.

6. The cleaning composition of claim 1, wherein the emulsifying agent is sunflower lecithin.

7. The cleaning composition of claim 1, wherein the wetting agent is selected from the group consisting of anionic wetting agents, cationic wetting agents, amphoteric wetting agents, and nonionic method wetting agents.

8. The cleaning composition of claim 1, wherein the wetting agent is sodium lauryl sulfoacetate.

* * * * *